(12) United States Patent
Frazier et al.

(10) Patent No.: US 7,048,723 B1
(45) Date of Patent: *May 23, 2006

(54) SURFACE MICROMACHINED MICRONEEDLES

(75) Inventors: A. Bruno Frazier, Mableton, GA (US); John D. Brazzle, Clearfield, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/787,498

(22) PCT Filed: Sep. 17, 1999

(86) PCT No.: PCT/US99/21509

§ 371 (c)(1),
(2), (4) Date: Mar. 16, 2001

(87) PCT Pub. No.: WO00/16833

PCT Pub. Date: Mar. 30, 2000

Related U.S. Application Data (60) Provisional application No. 60/101,064, filed on Sep. 18, 1998.

(51) Int. Cl.
*A61M 5/32* (2006.01)
(52) U.S. Cl. .................... 604/272; 604/273; 604/274
(58) Field of Classification Search ............ 604/272, 604/20, 191, 22, 35, 46, 501, 506, 181, 183, 604/239, 261, 186; 29/890.01, 890.1; 424/449, 424/483; 216/75, 100, 102

See application file for complete search history.

(56) References Cited

U.S. PATENT DOCUMENTS

| 3,964,482 | A | * | 6/1976 | Gerstel et al. ............ 604/890.1 |
| 4,285,779 | A | | 8/1981 | Shiga et al. .................... 204/9 |
| 4,493,753 | A | | 1/1985 | Becker et al. .................. 204/9 |
| 4,530,740 | A | | 7/1985 | Wolf et al. ..................... 204/9 |
| 4,707,225 | A | | 11/1987 | Schuler et al. ................. 204/9 |

(Continued)

FOREIGN PATENT DOCUMENTS

DE         WO97/03718  A1  *  2/1997

(Continued)

OTHER PUBLICATIONS

Chun, K. et al. Fabrication of Array of Hollow Microcapillaries Used for Injection of Genetic Material into Animal/Plant Cells, vol. 38, Issue 3, 1999.*

(Continued)

*Primary Examiner*—Henry Bennett
*Assistant Examiner*—Camtu Nguyen
(74) *Attorney, Agent, or Firm*—Workman-Nydegger (57) ABSTRACT

Surface micro-machined micro-needles (32) are formed as single needles (32) or in two-dimensional or three-dimensional micro-needle arrays (30). The micro-needles (32) are fabricated on a substrate (12) which can remain attached to the micro-needles (32) or can be subsequently removed. The two-dimensional or three-dimensional micro-needle arrays (30) can have cross-coupling flow channels (36) which allow for pressure equalization, and balance of fluid flow within the micro-needle arrays (30). Each of the micro-needles (32) has a micro-channel (36) therethrough that provides communication between at least one input port (37) at a proximal end of the micro-needles (32), and at least on output port (39) at an opposite distal end.

32 Claims, 7 Drawing Sheets

U.S. PATENT DOCUMENTS

| | | | |
|---|---|---|---|
| 4,728,392 A * | 3/1988 | Miura et al. | 216/27 |
| 4,780,395 A | 10/1988 | Saito et al. | 430/315 |
| 4,837,049 A | 6/1989 | Byers et al. | 427/96 |
| 4,871,623 A | 10/1989 | Hoopman et al. | 428/586 |
| 4,894,664 A | 1/1990 | Tsung Pan | 346/1.1 |
| 4,922,265 A | 5/1990 | Pan | 346/1.1 |
| 4,972,204 A | 11/1990 | Sexton | 346/75 |
| 5,194,877 A | 3/1993 | Lam et al. | 346/1.1 |
| 5,199,487 A | 4/1993 | DiFrancesco et al. | 165/168 |
| 5,249,358 A | 10/1993 | Tousignant et al. | 29/890.03 |
| 5,279,544 A * | 1/1994 | Gross et al. | 604/20 |
| 5,311,896 A | 5/1994 | Kaartinen | 137/15 |
| 5,312,456 A | 5/1994 | Reed et al. | 411/456 |
| 5,406,573 A * | 4/1995 | Ozbay et al. | 372/43 |
| 5,443,713 A | 8/1995 | Hindman | 205/70 |
| 5,457,041 A | 10/1995 | Ginaven et al. | 435/172.1 |
| 5,591,139 A | 1/1997 | Lin et al. | 604/264 |
| 5,611,806 A * | 3/1997 | Jang | 606/167 |
| 5,685,491 A | 11/1997 | Marks et al. | 239/533.12 |
| 5,762,811 A * | 6/1998 | Munoz | 216/11 |
| 5,855,801 A * | 1/1999 | Lin et al. | 216/2 |
| 5,871,158 A | 2/1999 | Frazier | 239/548 |
| 5,876,582 A | 3/1999 | Frazier | 205/122 |
| 5,928,207 A * | 7/1999 | Pisano et al. | 604/272 |
| 6,177,291 B1 * | 1/2001 | Eriguchi et al. | 438/42 |
| 6,256,533 B1 * | 7/2001 | Yuzhakov et al. | 604/21 |
| 6,334,856 B1 * | 1/2002 | Allen et al. | 345/562 |
| 6,379,324 B1 * | 4/2002 | Gartstein et al. | 604/22 |
| 6,397,466 B1 * | 6/2002 | Koyama et al. | 29/890.1 |
| 6,406,638 B1 * | 6/2002 | Stoeber et al. | 216/11 |
| 6,503,231 B1 | 1/2003 | Prausnitz et al. | |
| 6,511,463 B1 * | 1/2003 | Wood et al. | 604/272 |

FOREIGN PATENT DOCUMENTS

| | | | |
|---|---|---|---|
| JP | 2001-157715 | * | 9/2001 |
| WO | WO00/67647 A1 | * | 11/2000 |
| WO | WO01/33614 A1 | * | 5/2001 |

OTHER PUBLICATIONS

Tonucci, B et al. Nanochannel Array Glass, Science vol. 258 Oct. 1992.*

* cited by examiner

SURFACE MICROMACHINED MICRONEEDLES

This application claims the benefit of Provisional Application No. 60/101,064, filed Sep. 18, 1998.

BACKGROUND OF THE INVENTION

1. The Field of the Invention

The present invention relates generally to microneedles for the injection and extraction of fluids. More specifically, the present invention relates to an easily fabricated, micromachined array of microneedles or a single microneedle which can be easily attached to a syringe and which are mechanically durable.

2. The Relevant Technology

Micro instrumentation is a rapidly growing area of interest for a broad spectrum of engineering applications. One particularly fast growing area is biomedical instrumentation where significant efforts are being made to develop micro biochemical analysis systems, physiological systems, and drug delivery systems. A variety of manufacturing technologies are used to fabricate these micro systems, many of which are categorized under the set of technologies known as micromachining. The number of biomedical applications for micromachining technologies is rapidly growing. Since micromachining technologies are relatively new, there is an increasing set of manufacturing techniques and critical applications still to be addressed.

In many areas of biotechnology and medicine, there exists the need for fluid injection on a microscale; either for injection into a precise location, or for injecting small amounts of fluid. It is advantageous to be able to perform an injection with a minimal amount of tissue damage, and also with a minimum amount of discomfort and pain to patients. Microneedles and microneedle arrays are capable of performing these tasks. Some of the smallest hollow needles that are currently available have inner diameters of over 200 µm. Prior microsized (sizes on the order of microns, where 1 micron=1 µm=$10^{-6}$ m) needles have been made, as in U.S. Pat. No. 5,457,041 to Ginaven et al., and U.S. Pat. No. 5,591,139 to Lin et al.

For some applications, it is desirable to inject small amounts of fluid; however, in other situations, larger amounts of fluid are required to be injected. Most of the prior systems do not have the capability to transmit large amounts of fluid into a precise location. One of the methods used to address this problem is to fabricate an array of needles, as in U.S. Pat. No. 5,457,041 referred to hereinabove. The patent to Ginaven specifies an array of microneedles of about 20 needles by 20 needles, wherein the length of the needles is between 10 and 25 microns, and the spacing between needles is between about 5 and 20 microns.

Problems with prior microneedles include relatively poor mechanical durability. This is mainly due to the fact that such microneedles have been made out of etched silicon or out of chemical vapor deposited polysilicon, both of which have a tendency to be brittle and break easily.

It would therefore be of substantial interest to develop a durable device which is capable of injecting precise quantities of fluids into specific locations with a minimal amount of tissue damage, and which overcomes the difficulties associated with prior microneedle devices.

SUMMARY AND OBJECTS OF THE INVENTION

It is a primary object of the invention to provide an array of microneedles which is capable of transmitting relatively large quantities of fluids with minimal tissue damage and which can be readily attached to a standard syringe.

A further object of the invention is to provide an array of microneedles or a single microneedle which can be easily and economically fabricated according to standard micromachining procedures.

It is yet another object of the invention to provide an array of microneedles or a single microneedle which has a high degree of mechanical durability.

To achieve the forgoing objects and in accordance with the invention as embodied and broadly described herein, surface micromachined microneedles are formed as single needles or in two- or three-dimensional microneedle arrays. The microneedles are fabricated on a substrate which can remain attached to the microneedles or can be subsequently removed. The two- or three-dimensional microneedle arrays can have cross-coupling flow channels which allow for pressure equalization and balance of fluid flow within the microneedle arrays. Additionally, a plurality of mechanical support members can be integrated into the arrays for stability and to control the penetration depth of the microneedles.

In one embodiment of the invention, a microneedle array device includes a substrate having a substantially planar surface, and a plurality of hollow non-silicon microneedles on the planar surface of the substrate. Each of the microneedles has a microchannel therethrough that provides communication between at least one input port at a proximal end of each of the microneedles and at least one output port at an opposite distal end that extends beyond an edge of the substrate.

A method of fabricating a microneedle device according to the present invention includes providing a substrate with a substantially planar surface, and depositing a metal material on the planar surface to form one or more bottom walls for one or more microneedles. A top surface of the bottom walls is coated with a photoresist layer to a height corresponding to a selected inner height of a microchannel for each of the microneedles. A metal material is then deposited to form side walls and a top wall upon the bottom walls and around the photoresist layer. The photoresist layer is then removed from each microchannel to form the microneedles. The microneedles can be released from the substrate and used independent of the substrate, if desired.

The method of fabricating the microneedle device can include $p^+$ etch-stop membrane technology, anisotropic etching of silicon in potassium hydroxide, sacrificial thick photoresist micromolding technology, and micro-electrodeposition technology.

These and other objects and features of the present invention will become more fully apparent from the following description, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

The present invention is directed to micromachined arrays of microneedles and single microneedles which exhibit mechanical durability. The microneedles are capable of injecting precisely controlled amounts of fluid, and can be easily and economically fabricated according to standard micromachining procedures.

Referring to the drawings, wherein like structures are provided with like reference designations, the drawings only show the structures necessary to understand the present invention. Additional structures known in the art have not been included to maintain the clarity of the drawings.

Figure 1:
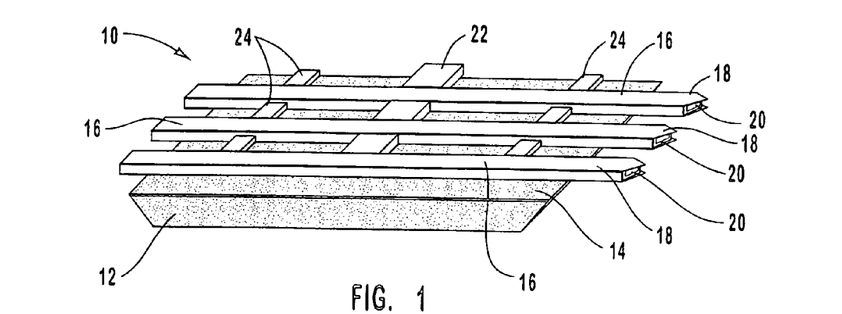
FIG. 1 is a schematic representation of microneedles in a two-dimensional array according to one embodiment of the present invention.

A schematic depiction of a micromachined needle array 10 according to one embodiment of the invention is shown in FIG. 1. The needle array 10 is formed in a two-dimensional configuration on a substrate 12 having a substantially planar upper surface 14. The substrate 12 is preferably composed of a semiconductor material such as silicon, although other materials can be employed such as glass, metals, ceramics, plastics, and composites or combinations thereof.

A plurality of fluidly interconnected hollow microneedles 16 are formed on upper surface 14 of substrate 12. The microneedles 16 each have a bottom wall, two opposing side walls, and a top wall that define a microchannel therein. This provides the microchannel with a transverse cross-sectional profile that is substantially rectangular. Each bottom wall is formed partially on upper surface 14 of substrate 12. The microneedles each have one or more input ports in an input shaft, and a portion of each microneedle 16 including the microchannels extends beyond an edge of upper surface 14 of substrate 12 in a cantilevered section which terminates in a needle tip 18 with a channel opening 20 therein. The microneedles 16 are preferably aligned substantially parallel to each other on substrate 12.

The microchannels in the microneedles 16 are preferably dimensioned to have a width between sidewalls of less than about 100 μm, and more preferably about 0 μm to about 50 μm. When the width is zero between the sidewalls, the microneedles 16 effectively become one multilumen microneedle with a plurality of microchannels. The height between the top and bottom walls of the microchannel is also preferably less than about 100 μm, and more preferably about 2 μm to about 50 μm. The length of each microneedle can be from about 0.05 μm to about 5 mm, and the width of each microneedle can be from about 0.05 μm to about 1 mm. The center-to-center spacing between individual microneedles can be from about 50 μm to about 200 μm. The microneedles can also withstand flow rates of up to about 1.5 cc/sec.

The microneedle length extended from the substrate can be varied from less than about 50 μm (subcutaneous) to several millimeters for fluid delivery/extraction. For example, the distal end of each microneedle can extend beyond the edge of the substrate a distance from about 10 μm to about 100 mm. The inner cross-sectional dimensions of the microchannels in individual needles can range from about 10 μm to about 1 mm in width and about 2 μm to about 50 μm in height. Accordingly, the microchannel in each of the microneedles can have a cross-sectional area in the range from about 25 μm$^2$ to about 5000 μm$^2$.

A needle coupling channel member 22 is also formed on upper surface 14 of substrate 12 between microneedles 16. The coupling channel member 22 has a bottom wall, two opposing side walls, and a top wall that define a coupling microchannel therein, which provides for fluid communication between the microchannels of each microneedle 16. The coupling channel member 22 also allows for pressure equalization and balance of fluid flow between microneedles 16.

A pair of structural support members 24 are formed on either side of coupling channel member 22 on upper surface 14 of substrate 12. The structural support members 24 mechanically interconnect microneedles 16 to provide rigidity and strength to needle array 10. The support members 24 also precisely control the penetration depth of microneedles 16.

The microneedles 16, coupling channel member 22, and support members 24 can be formed from a variety of metal materials such as nickel, copper, gold, palladium, titanium, chromium, alloys or combinations thereof, and the like, as well as other materials such as plastics, ceramics, glass, carbon black, composites or combinations thereof, and the like. The microneedles can be in fluid communication with a single fluid input device or with multiple fluid input devices.

Figure 2A:
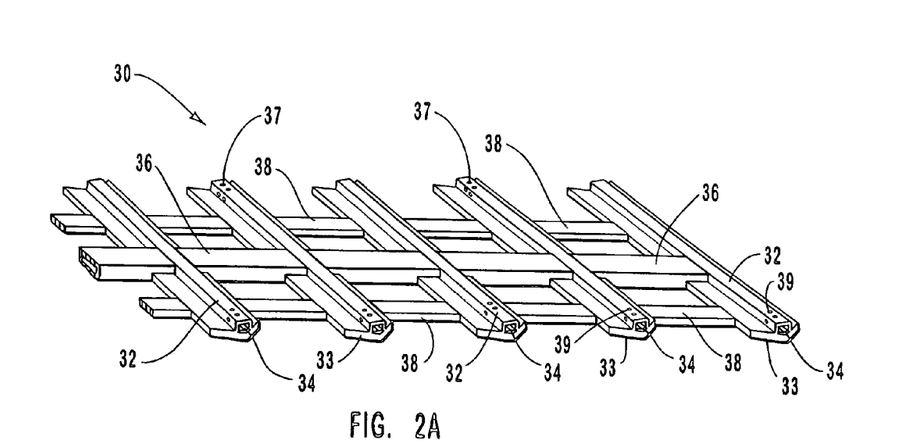
FIG. 2A is a schematic representation of microneedles in a two-dimensional array according to another embodiment of the present invention.

A micromachined needle array 30 according to another embodiment of the invention is shown in FIG. 2A. The needle array 30 has a two-dimensional configuration with similar components as needle array 10, except that the substrate has been removed from the array. Accordingly, needle array 30 includes a plurality of microneedles 32 with microchannels therein that are dimensioned as discussed above for needle array 10. The microneedles 32 each terminate at a needle tip 33 with a channel opening 34 therein. A needle coupling channel member 36 with a coupling microchannel therein provides a fluidic interconnection between the microchannels of each microneedle 32. A pair of structural support members 38 are formed on either side of coupling channel member 36 and interconnect with microneedles 32. One or more input ports 37 and output ports 39 can be optionally formed in microneedles 32 to increase fluid input and output flow. The input ports 37 and output ports 39 can be formed in one or more of the bottom wall, side walls, or top wall of microneedles 32 by conventional fabrication processes such as etching.

Figure 2B:
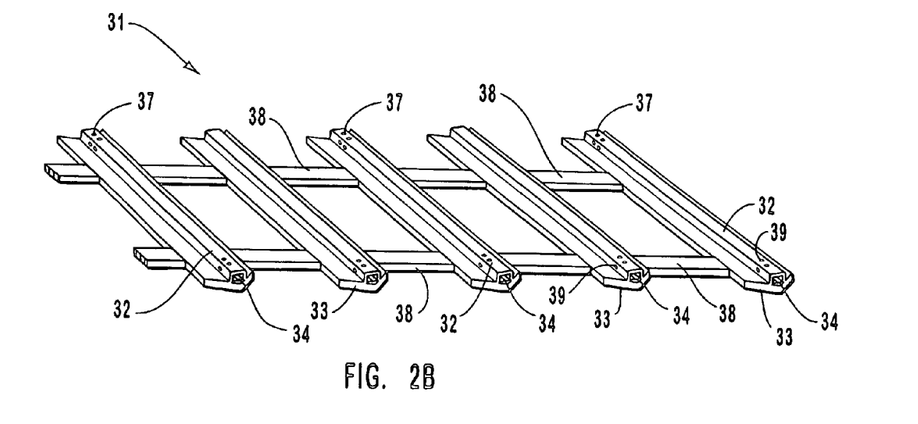
FIG. 2B is a schematic representation of microneedles in a two-dimensional array according to another embodiment of the present invention.

A micromachined needle array 31 according to another embodiment of the invention is shown in FIG. 2B. The needle array 31 has a two-dimensional configuration with similar components as needle array 30, except that needle array 31 is formed without a coupling channel member. Accordingly, needle array 31 includes a plurality of microneedles 32 with microchannels therein that are dimensioned as discussed above for needle array 10. The microneedles 32 each terminate at a needle tip 33 with a channel opening 34 therein. A pair of structural support members 38 interconnect with microneedles 32. One or more input ports 37 and output ports 39 can be optionally formed in microneedles 32 to increase fluid input and output flow.

Figure 3:
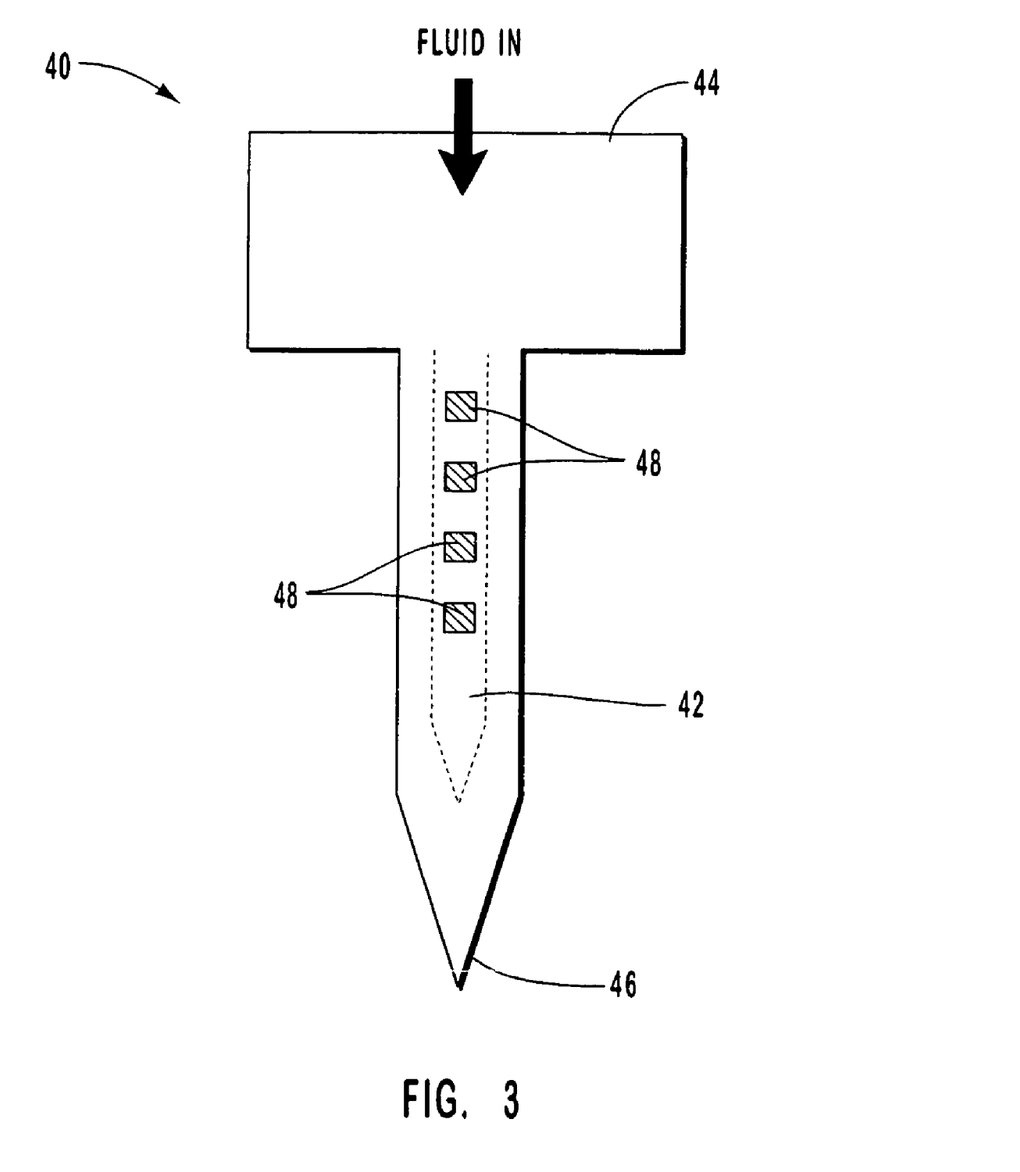
FIG. 3 is a schematic representation of a single microneedle according to a further embodiment of the present invention.

FIG. 3 is a schematic representation of a single hollow microneedle 40 according to a further embodiment of the present invention which can be fabricated by standard micromachining techniques. The microneedle 40 has a bottom wall, two opposing side walls, and a top wall that defines a microchannel 42 therein. The microchannel 42 communicates with a flanged inlet end 44 for fluid input. The flanged inlet end 44 can include single or multiple fluid input ports and acts as a structural support for microneedle 40. The flanged inlet end 44 can control penetration depth and can be used to mechanically fix microneedle 40 to a surface that is penetrated. The microneedle 40 terminates at a needle tip 46 at an opposite end from inlet end 44. One or more output ports 48 are formed in microneedle 40 between inlet end 44 and needle tip 46. The output ports 48 can be formed in one or more of the bottom wall, side walls, or top wall of microneedle 40 by conventional fabrication processes such as etching. The microneedle 40 can be formed from a variety of materials such as nickel, copper, gold, palladium, titanium, chromium, alloys thereof, and the like, as well as other materials such as plastics, ceramics, glass, carbon black, composites thereof, etc. The microneedle 40 can be on a substrate as shown for the array of FIG. 1, or can be removed from a substrate as shown for the array of FIG. 2A.

Figure 4A:
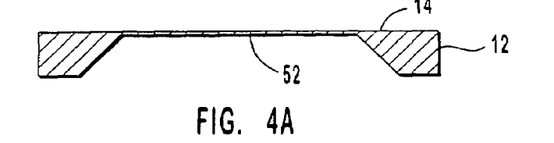
FIGS. 4A–4F depict schematically the fabrication process sequence for forming a microneedle array.

A method of fabricating a two-dimensional needle array according to the invention is depicted schematically in FIGS. 4A–4F. As shown in FIG. 4A, a substrate 12 having a substantially planar surface 14 is provided, such as a silicon wafer which is polished on both sides. The wafer can have a thickness of about 1 μm to about 700 μm, and is preferably about 150 μm thick. One side of the wafer is heavily doped with boron using high temperature thermal diffusion in order to form a 3–5 μm thick p+ layer. Next, silicon nitride ($Si_3N_4$) is deposited on both sides of the wafer using plasma-enhanced chemical vapor deposition (PECVD). The silicon nitride on the undoped side of the wafer is patterned and etched employing photoresist as a mask, and then isotropic etching (a $CF_4$ plasma for example) is used to etch the exposed silicon nitride to define the area upon which the microneedles are to be fabricated. After patterning the silicon nitride layer, the exposed silicon is anisotropically etched using a potassium hydroxide (KOH) solution. The p+ boron layer serves as an etch stop, resulting in a thin sacrificial membrane 52, as shown in FIG. 4A. The sacrificial membrane 52 comprises the surface upon which the microneedles are formed and then subsequently released as described below.

Figure 4B:
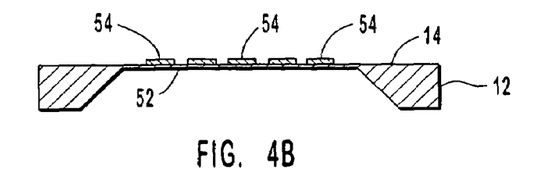

Next, a metal system of adhesion layers and an electroplating seed layer are deposited (by electron beam evaporation, for example) onto the insulating silicon nitride film. The adhesion and seed layers are typically composed of, but not limited to, titanium, chromium, copper, or combinations thereof. Then, using a mask of the appropriate dimensions and standard photolithographic techniques, this metal multilayer is patterned. A metal material is then electroplated to form one or more bottom walls 54 (e.g. about 20 μm thick) for the microneedles, as shown in FIG. 4B. Palladium is a preferred metal for the bottom wall since it provides high mechanical strength and durability, is corrosion resistant, provides biocompatibility for use in biomedical applications, and is easily electroplated to within precise dimensions. Other materials which fit the criteria mentioned could also be used equally well, such as copper, nickel, or gold. When performing the electroplating, the bath chemistry and the electroplating conditions (such as amount of applied current and time in the electroplating bath) should be precisely controlled for optimum results. The typical dimensions for bottom walls 54 are about 10–20 μm in thickness, and about 50 μm wide.

Figure 4C:
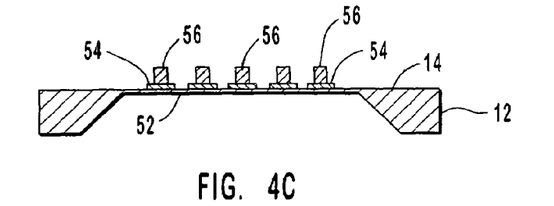

After bottom walls 54 have been formed, a commercially available thick photoresist is deposited (e.g., about 20 μm thick) and patterned using ultraviolet exposure and alkaline developer, resulting in sacrificial layers 56 as depicted in FIG. 4C. Next, a metal seed layer such as gold is sputter deposited (e.g., about 800 Å thick) onto the photoresist sacrificial layers 56. The metal seed layer serves as an electrical contact for the subsequent metal electroplating.

Figure 4D:
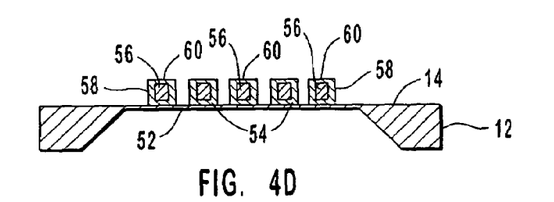
Figure 4E:
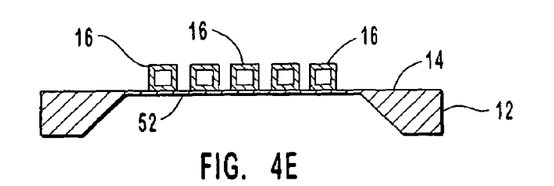

A metal layer is then electroplated (e.g., about 20 μm thick) onto sacrificial layers 56 to form the a plurality of side walls 58 and top walls 60 of each microneedle, as shown in FIG. 4D. The exposed metal seed layer is then removed using wet etching techniques to expose the underlying photoresist. Once the metal seed layer has been etched, the wafer is placed in an acetone bath to remove the thick photoresist from inside the microneedle structures, thereby producing a plurality of hollow microneedles 16, as shown in FIG. 4E.

Figure 4F:
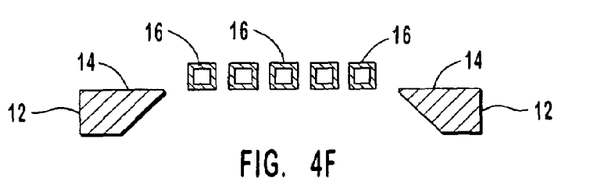

In the final processing step, sacrificial membrane 52 is removed by an isotropic etching technique, such as reactive ion etching in a $SF_6$ plasma. Thus, the microneedle ends are released from sacrificial membrane 52 and are freely suspended, projecting outward from substrate 12, as depicted in FIG. 4F and in the embodiment of FIG. 1.

In addition, the needle arrays can be released from substrate 12 following surface fabrication on substrate 12, if desired, such as in the embodiment shown in FIG. 2A. This method does not require sacrificial membrane formation or KOH etching. Instead, the needle arrays are released using wet etching of the seed metal from underneath the needle structures. If the seed metal is copper, for example, then this can be done by a selective etch of ammonium hydroxide saturated with cupric sulfate.

The support members and needle walls formed by microelectroforming processes provide increased structural integrity. In addition, the needle coupling channels minimize the effects of restricted needle passages by providing a redistribution point for fluid flow between the passages.

Arrays of two up to hundreds of microneedles can be easily and economically fabricated in a package with dimensions on the order of millimeters according to the above procedure. A single microneedle such as shown in FIG. 3 can also be fabricated according to the procedure outlined above. In addition, instead of having the fluid outlet at the tips of the microneedles, fluid outlet ports can be etched into the side walls, top walls, and/or bottom walls of the microneedle(s) if a larger amount of fluid transfer is desired.

Figure 4G:
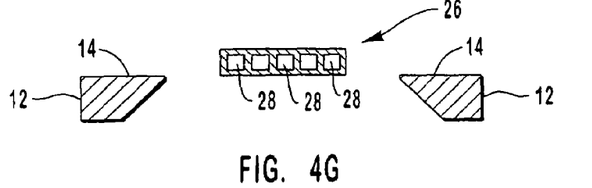
FIG. 4G depicts an embodiment of a multilumen microneedle formed according to the present invention.

Alternatively, the fabricating method outlined above can be used to form a multilumen microneedle by forming bottom walls 54 with zero spacing therebetween on substrate 12 and carrying out the remaining steps as described above. A resulting multilumen microneedle 26 with a plurality of microchannels 28 is shown in FIG. 4G.

All of the microneedles and arrays of the present invention can be coated on the inside with biocompatible materials, such as silicon nitride, gold, plastics etc., by conventional coating processes known to those skilled in the art.

Figure 5A:
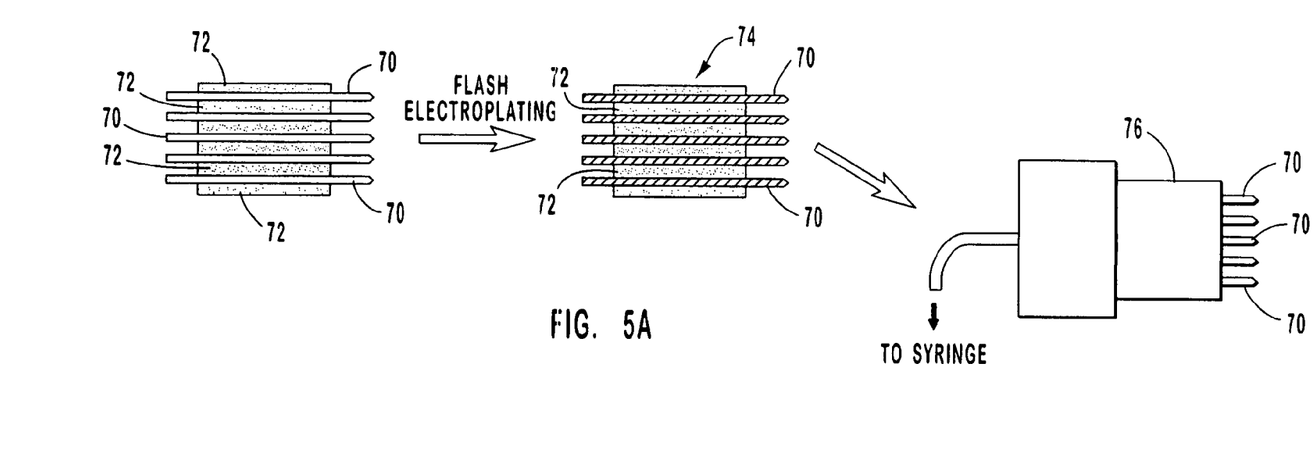
FIGS. 5A and 5B depict alternative methods of assembling two-dimensional needle arrays into three-dimensional needle array devices.

FIGS. 5A and 5B depict alternative methods of assembling two-dimensional needle arrays into three-dimensional needle array devices. In the method depicted in FIG. 5A, a plurality of two-dimensional needle arrays 70 are provided which have been released from a substrate as shown for the array of FIG. 2A. The needle arrays 70 are positioned in a stacked configuration with a plurality of metallic spacers 72 therebetween to define the distance between any two microneedle arrays in the stack. The stacked needle array configuration is then subjected to flash electroplating to join needle arrays 70 with metallic spacers 72 in a fixed three-dimensional needle array device 74. The an acrylic interface, allowing connection to a dispensing means for injecting a liquid such as a syringe.

Figure 5B:
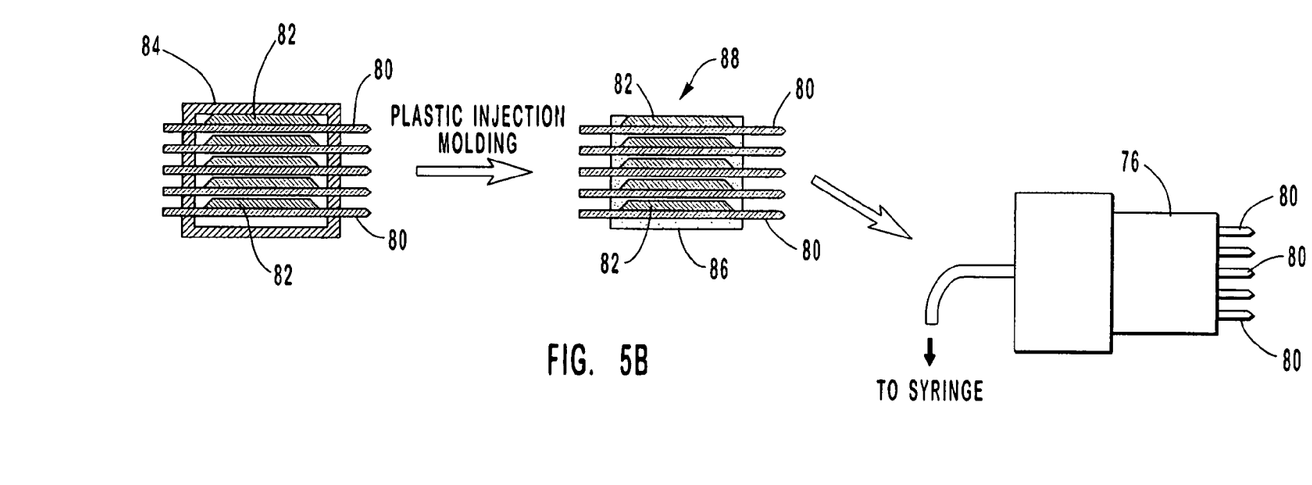

In the method depicted in FIG. 5B, a plurality of two-dimensional needle arrays 80 are provided on substrates 82 such as shown for the array of FIG. 1. The needle arrays 80 are positioned in a stacked configuration with substrates 82 acting as spacers between the arrays 80, to define the distance between any two microneedle arrays in the stack. The stacked needle array configuration is placed in a mold 84 such as an aluminum mold for plastic injection molding. The stacked needle array configuration is then subjected to plastic injection molding. This bonds needle arrays 80 together with a plastic molding material 86, thereby forming a fixed three-dimensional needle array device 88. The needle array device 88 can then be disposed in an interface structure 76 allowing connection to a dispensing device such as a syringe.

In another alternative method of assembling two-dimensional needle arrays into three-dimensional needle array devices, the two dimensional arrays are manually assembled under a microscope. The two-dimensional arrays are stacked with spacers or with substrates on the arrays and are bonded together with a polymeric adhesive such as a UV-curable adhesive to form a three-dimensional needle array device, which can then be disposed in an interface structure.

The fabricated three-dimensional needle array devices are typically dimensioned to have a length of about 5 mm, a width of about 5 mm, and a height of about 2 mm.

The interface structures for connection to a syringe can be made from a variety of plastic materials such as acrylics, polystyrene, polyethylene, polypropylene, and the like. The interface structure typically accommodates a three-dimensional needle array device having up to about 25 two dimensional arrays. The interface structures are bonded to the three-dimensional needle array devices with a polymeric adhesive such as a UV-curable adhesive. The interface structures are configured to accept direct syringe connection via a connection means such as a conventional Luer-lock connector. Alternatively, interface structures can be formed for a single two-dimensional array or a single microneedle so as to accept direct syringe connection via a connector such as a Luer-lock connector.

The micromachined microneedles of the invention have many benefits and advantages. These include reduced trauma at penetration sites due to their small size, greater freedom of patient movement because of the minimal penetration depth of the needles, a practically pain-free drug delivery due to the smaller cross section of the needle tip and distribution of fluid force, and precise control of penetration depth from needle extension length. In addition, the microneedles have the ability to deliver drugs to localized areas, and are advantageous in their ability to be stacked and packaged into a three-dimensional device for fluid transfer.

The micromachined microneedles can be used in a wide variety of biomedical applications. The microneedles can withstand typical handling and can subcutaneously deliver medication without the usual discomfort associated with conventional needles. The microneedles are minimally invasive, in that the microneedles only penetrate just beyond the viable epidermis, reaching the capillaries and minimizing the chance of encountering and damaging the nerves present in the area of penetration.

The following examples are given to illustrate the present invention, and are not intended to limit the scope of the invention.

EXAMPLE 1

A two dimensional microneedle array was fabricated according to the procedure outlined above to have to have 25 microneedles. The inner dimensions of the hollow microneedles were made to be of inner cross-sectional area of $40 \times 20$ $\mu m^2$ (width by height) and outer cross-sectional area of $80 \times 60$ $m^2$. The needle coupling channels were 100 $\mu m$ wide, and provided fluid communication between each needle channel. Two sets of $60 \times 100$ $\mu m^2$ structural supports were located 250 $\mu m$ from each needle end. Each needle channel was 2 mm long, while the width of the 25 needle array was 5.2 mm. The center-to-center spacing between individual needles was 200 $\mu m$. The needle wall thickness was approximately 20 $\mu m$ of electroformed metal.

Needle arrays were fabricated from electroformed low stress nickel sulphamate, gold cyanide, and palladium electroforming solutions. The bath chemistry and electroplating conditions were selected and precisely controlled to allow formation of low stress depositions on top of a 3–5 $\mu m$ sacrificial membrane. The surface roughness of the electroplated metals was found by Atomic Force Microscope (AFM) to be approximately 15 nm, resulting in a relative roughness of 0.00056.

It is important to note the structural quality of the needle tips. The inner dimensions were approximately $30 \times 20$ $\mu m^2$, outer dimensions were approximately $80 \times 60$ $\mu m^2$, and the needle tips were formed with 45° angles for ease of penetration.

EXAMPLE 2

Analytical and computer modelling were performed in order to assess how the cross-flow design feature unique to this invention can be used to equalize the pressure distribution across the needle channels, to generally determine the relationships between input pressure and fluid delivery rates for the array, and to investigate the interrelationships amongst the physical dimensions of the needle array. The purpose of the model is (a) to determine the relationship between the input pressure and the fluid delivery rates for the microneedle array and (b) to investigate the relationships between the physical dimensions of the microneedle array (cross-sectional areas of the primary and coupling channels) and the effect on restricted flow within the microneedle array. Pressure equalization may become necessary in the event that some of the individual needle channels become obstructed. The model described herein can be used to characterize the fluid flow rates throughout the micromachined needle array and to determine the most effective design dimensions.

The general equation that governs the motion of a viscous compressible fluid in Cartesian coordinates can be expressed as:

$$\mu\nabla^2 V - \nabla p + \rho f = \rho \dot{V} \quad (1)$$

where a superimposed dot indicates a material derivative, V is the fluid velocity vector, f represents the external forces (such as gravity, for example) μ is the fluid viscosity, and ∇p is the pressure gradient required to move the fluid. The equation is known as the Navier-Stokes equation. For the case of a Newtonian fluid with uniform physical properties (water, for example) and negligible effects from external forces moving through a rectangular channel, the flow is two-dimensional and can be simplified to:

$$\frac{\partial^2 V}{\partial x^2} \cdot \frac{\partial^2 V}{\partial y^2} - \frac{1}{\mu}\nabla p = 0 \quad (2)$$

where x is the direction along the microchannel width and y is the direction along the microchannel height.

These equations were solved numerically using commercially developed ANSYS software, which is based on the finite element method (FEM). The elements used in this numerical model are solved for flow distributions within a region, as opposed to elements that model a network of one dimensional regions hooked together. A segregated sequential solver algorithm is used; that is, the matrix system derived from the finite element discretization of the governing equation for each degree of freedom is solved separately. The degrees of freedom in this case are velocity, pressure, and temperature.

The flow problem is inherently nonlinear, and the governing equations are coupled together. The sequential solution of all the governing equations, combined with the update of any pressure dependent properties, constitutes a global iteration. The number of global iterations required to achieve a converged solution in this analysis was 15, implying that the model is stable.

The numerical model is solved for an array of 10 microneedles. Each needle channel is 40 μm in width and 2 mm long, while the needle coupling channels which interconnect each needle channel are 100 μm in width. The vectors that run along the center of each needle channel depict the highest fluid flow rate (1.459 cc/sec), while the small vectors in the middle of each needle coupling channel depict a zero fluid flow rate. The pressure drop across the length of each individual needle was 16.2 kPa. The model was fairly successful at illustrating the effect that the needle coupling channels have on the rest of the system. The model indicates that an equilibrium in the fluid interaction within the needle coupling channels is obtained and that the fluid flow within the needle coupling channels appears not to interfere with the fluid flow in the needle channels.

Figure 6A:
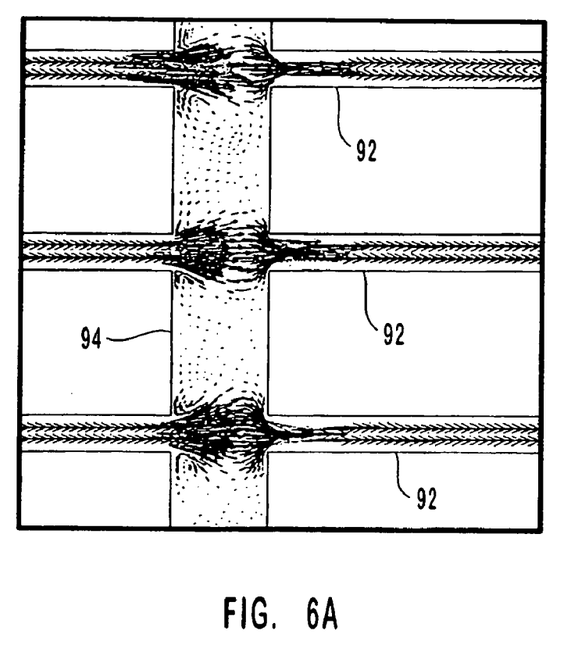
FIGS. 6A–6C are vector magnitude plots showing the effects of fluid flow rate on needle coupling channels and needle channels.

The effect that the needle coupling channels have on the rest of the system is shown in the vector magnitude plot of FIG. 6A. This plot shows the magnitude of the fluid rate components, with the vectors in the middle of each needle channel 92 representing the greatest magnitude (1.471 cc/sec), while the small vectors in the center of each needle coupling channel 94 represent a vector magnitude of zero. The fluid flow rates remain static within the needle coupling channels when there is no opposition (i.e., clog) to the flow within the needle channels. The input needle channels (indicated on the left in FIG. 6A) have the same fluid flow rate as the output needle channels (indicated on the right of FIG. 6A).

Figure 6B:
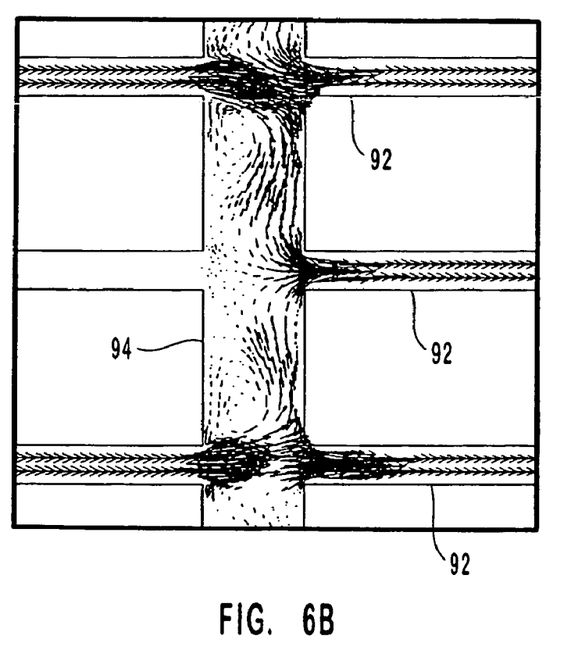

The effects on flow characteristics when a needle becomes clogged can be seen in FIG. 6B. FIG. 6B is a vector plot of the flow in needle channels 92 when one input is obstructed. The model indicates that the flow in the channel adjacent to the clogged needle is augmented by the incoming fluid flow from other needle channels by means of the needle coupling channels. Flow within the needle coupling channel 94 is as high as 0.912 cc/sec. The overall flow rate through the array remains constant due to conservation of mass. However, the flow rate within the individual output needle channels is decreased to compensate for the clogged passage. The flow rate in the input needle channels is 1.459 cc/sec, while the flow rate in the output channels is 1.276 cc/sec. This indicates a 14.3 percent decrease in the flow rate in individual needle channels. In addition, a developing flow region is present at the entrance of the output needle channel, extending approximately 100 μm from the needle coupling channel, while this figure shows the interaction between only three needle channels, the needle coupling channels redistribute fluid throughout the entire array. It was found that all of the fluid flow rates were identical in all of the output needle channels with an accuracy of 0.0001 cc/sec.

Figure 6C:
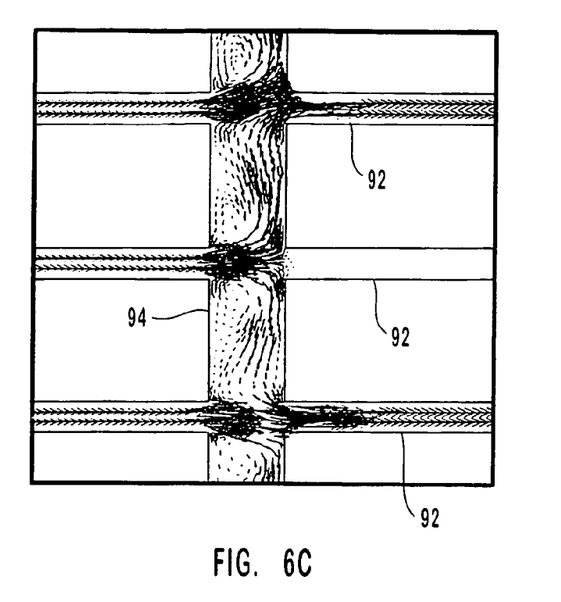

In the event that an obstruction is encountered in one of the output needle channels, the result is similar, with the exception that fluid flow from the unobstructed input needle channels would then be redistributed to the unobstructed output needle channels. FIG. 6C shows a vector plot illustrating the effect that the needle coupling channel 94 has on the needle channels 92 when an output is obstructed. The flow in the needle channels adjacent to the clog act to augment the outgoing fluid flow to the other needle channels by means of the needle coupling channels. Flow within the needle coupling channels is as high as 0.831 cc/sec. The overall flow rate through the needle array again remains constant due to conservation of mass. However, the flow rate within the individual output needles is increased to compensate for the clogged passage. The flow rate in the input needle channels is 1.246 cc/sec., while the flow rate in the output needle channels is 1.453 cc/sec. This indicates a 16.6% increase in the flow rate in individual needle channels. In addition, a developing flow region is present at the entrance of the output needle channel, extending approximately 100 μm from the needle coupling channel. The flow rates in the output needle channels are the same to within an accuracy of 0.0001 cc/sec.

The ANSYS model successfully characterized the flow in the microchannels using the specified dimensions. In FIG. 6A, the flow within the needle coupling channels remains static, while in FIGS. 6B and 6C, the flow within the needle coupling channels dynamically tends towards the needle channels of less resistance. Fluid flow rates within the needle coupling channels adjacent to the obstruction showed an increase of 90%, while the fluid flow rates at the far end of the array showed an increase of less than 10%. The fluid flow rates in individual needle channels show an increase or decrease depending on the location of the obstruction. The needle coupling channels, therefore, act to redistribute the fluid flow as necessary when needle inputs or outputs are clogged.

EXAMPLE 3

Figure 7:
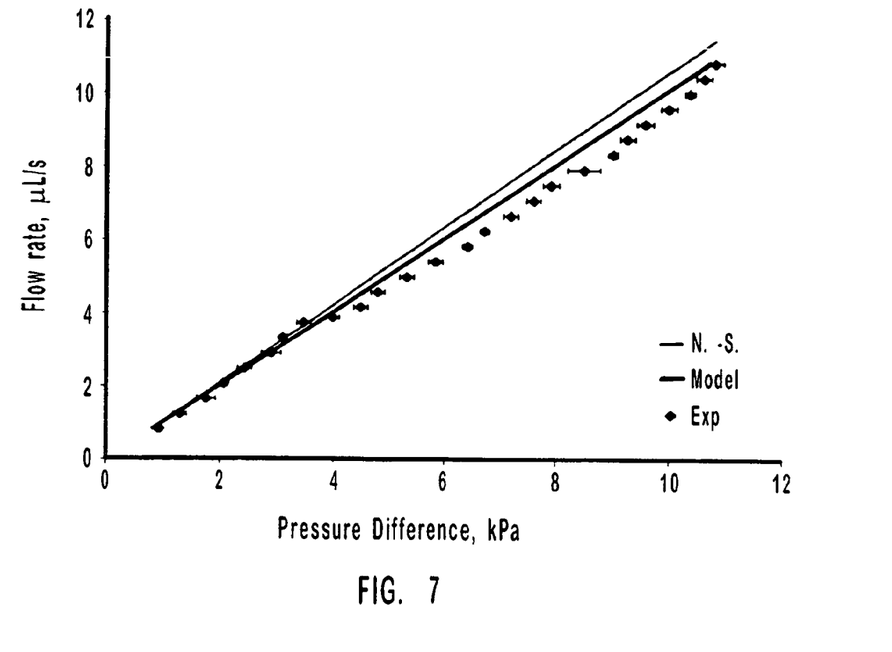
FIG. 7 is a graph of the flow rate as a function of pressure difference for a microneedle array of the invention.

Flows in channels of similar dimensions were compared experimentally. FIG. 7 represents data for flow of water in 3000×600×30 µm³ (length×width×height). The microchannels in this example were fabricated according to the procedures described previously. The plot of the data in FIG. 7 serves to show the agreement between the data and the predictions of the Navier-Stokes (N-S) theory and the model based on the micropolar fluid theory.

EXAMPLE 4

Five packaged microneedles were fabricated according to the procedures described hereinabove. Fluid flow rate tests were conducted to determine the rate of flow through each packaged microneedle as a function of pressure. Each microneedle was attached to a standard 5 cc syringe filled with water and affixed vertically in a test stand. The test stand was positioned in proximity to an Instron (model 4400) load frame so that the calibrated load cell would come in contact with the syringe plunger. The load frame has the capability of maintaining a constant force on the syringe plunger over specified periods of time. Prior to each test, a sealed flask was placed on a scale and zeroed. The flask was filled and kept at a constant level to keep the surface area of the water nearly constant. This method helps to maintain a constant rate of evaporation, which was also monitored during the tests. The load frame was set to apply a constant force over a period of thirty minutes, while the sealed flask was used to capture the water dispensed by the syringe. After the thirty minute period, the load was removed and the flask was placed on a scale to measure the resultant amount of water that had accumulated. The scale (Sartorius model 1602 MP8-1) was enclosed in a glass case and has a resolution of 100 µg. The evaporation rate was checked prior to each test by placing the sealed flask on the scale and noting the weight loss over a period of thirty minutes. The value obtained was then added to the resultant data from the needle tests.

The dimensions of each needle shaft were 200 µm wide and 60 µm thick, and the tip dimensions were less than 15×15 µm². The length of the tapered portion was 1 mm and the distance from the tip to the first output port was approximately 300 µm. The total length of the microneedles was 6 mm, with inner channel dimensions of 140 µm wide and 20 µm high. The wall thickness of each needle was approximately 20 µm and the microneedle output ports were on the top and bottom with dimensions of 30 µm². The output ports were separated by 30 µm and there were nine ports on the top and 12 ports on the bottom.

Figure 8:
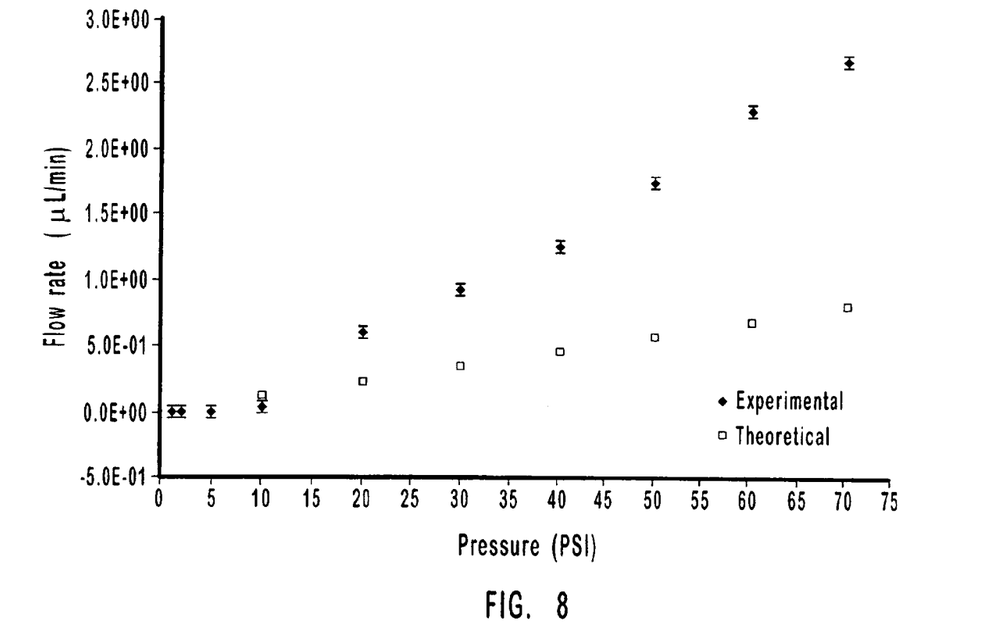
FIG. 8 is a graph of the flow rate as a function of pressure for five individual microneedles of the invention.

The fluid flow experiments were performed on the five packaged microneedles at pressures ranging from 1 to 70 psi. The fabricated needles were packaged into an interface using UV-curable epoxy. Pressures were applied to each microneedle at 30 minute intervals while the weight of the water that had accumulated during each test was recorded. The weight data was converted into fluid flow rates for the needles based on the density of water at 25° C. and the results are shown in the graph of FIG. 8. The microneedles demonstrated flow rates in the range of 0.00384 to 2.67 µL/min with applied pressures of 1 to 70 psi. The packaged microneedles also exhibited the ability to withstand pressures exceeding 100 psi.

The theoretical data were obtained by repeating the previously described models for the same input pressures that were used in the fluid flow tests. The theoretical data are also plotted in FIG. 8; however, the resultant data do not accurately predict the experimentally obtained fluid flow rates. One possible explanation for the discrepancy in flow rates is that the presence of microscale surface effects, such as rotations of molecules, variations of viscosity, slip velocity, and capillary effects were not accounted for in the theoretical calculations.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A microneedle array device, comprising:
a substrate having a substantially planar first surface and an edge adjacent said substantially planar first surface; and
a plurality of hollow non-silicon microneedles positioned on said substantially planar first surface of said substrate, each of said hollow non-silicon microneedles having a microchannel therethrough providing communication between at least one input port at a proximal end of each of said hollow non-silicon microneedles and at least one output port at a distal end of each of said hollow non-silicon microneedles, wherein said hollow non-silicon microneedles extend beyond said edge of said substrate and extend in a direction substantially parallel to said substantially planar first surface.

2. The microneedle array device of claim 1, wherein said hollow non-silicon microneedles each have a bottom wall, two side walls, and a top wall defining a microchannel.

3. The microneedle array device of claim 2, wherein said bottom wall is formed at least partially on top of said substantially planar first surface of said substrate and said side walls and top wall are formed around a removable molding material.

4. The microneedle array device of claim 1, wherein said hollow non-silicon microneedles comprise a two dimensional array.

5. The microneedle array device of claim 1, wherein said hollow non-silicon microneedles comprise a three dimensional array.

6. The microneedle array device of claim 5, wherein said three dimensional array comprises a plurality of two dimensional arrays with spacers therebetween.

7. The microneedle array device of claim 6, wherein said three dimensional array is bonded together by a material selected from the group consisting of molding materials, polymeric adhesives, and combinations thereof.

8. The microneedle array device of claim 1, wherein said hollow non-silicon microneedles are aligned substantially parallel to each other on said substrate.

9. The microneedle array device of claim 1, wherein the distal end of each said hollow non-silicon microneedle extends beyond said edge of said substrate a distance from about 10 µm to about 100 mm.

10. The microneedle array device of claim 1, wherein said microchannel in each of said hollow non-silicon microneedles has a cross-sectional area in the range from about 25 µm² to about 5000 µm².

11. The microneedle array device of claim 1, wherein the length of each said hollow non-silicon microneedle is from about 0.05 μm to about 5 mm, and the width of each said hollow non-silicon microneedle is from about 0.05 μm to about 1 mm.

12. The microneedle array device of claim 1, wherein the center-to-center spacing between individual said hollow non-silicon microneedles is from about 50 μm to about 200 μm.

13. The microneedle array device of claim 1, wherein said substrate comprises a material selected from the group consisting of glass, semiconductor materials, metals, ceramics, plastics, and composites or combinations thereof.

14. The microneedle array device of claim 1, wherein said hollow non-silicon microneedles comprise a material selected from the group consisting of metals, plastics, ceramics, glass, carbon black, and composites or combinations thereof.

15. The microneedle array device of claim 1, wherein said hollow non-silicon microneedles comprise a metal material selected from the group consisting of nickel, copper, gold, palladium, titanium, chromium, and alloys or combinations thereof.

16. The microneedle array device of claim 1, wherein said hollow non-silicon microneedles can withstand flow rates of up to about 1.5 cc/sec.

17. The microneedle array device of claim 1, further comprising a coupling channel member providing fluid communication between said hollow non-silicon microneedles.

18. The microneedle array device of claim 17, wherein said coupling channel member is composed of the same material as said hollow non-silicon microneedles.

19. The microneedle array device of claim 1, further comprising a pair of structural support members mechanically interconnecting said hollow non-silicon microneedles and precisely controlling penetration depth of said hollow non-silicon microneedles.

20. The microneedle array device of claim 1, wherein said hollow non-silicon microneedles have a plurality of input ports.

21. The microneedle array device of claim 1, wherein said hollow non-silicon microneedles have a plurality of output ports.

22. A microneedle device, comprising:
a substrate having a substantially planar first surface and an edge adjacent said substantially planar first surface; and
a single hollow non-silicon microneedle positioned on said substantially planar first surface of substrate, said hollow non-silicon microneedle having at least one microchannel therethrough providing communication between at least one input port at a proximal end of said hollow non-silicon microneedle and at least one output port at distal end of said hollow non-silicon microneedle, the distal end of said hollow non-silicon microneedle extending beyond said edge of said substrate, wherein said hollow non-silicon microneedle extends in a direction substantially parallel to said substantially parallel first surface.

23. The microneedle device of claim 22, wherein the distal end of said hollow non-silicon microneedle extends beyond said edge of said substrate a distance from about 10 μm to about 100 mm.

24. The microneedle device of claim 22, wherein said microchannel in said hollow non-silicon microneedle has a cross-sectional area in the range from about 25 μm$^2$ to about 5000 μm$^2$.

25. The microneedle device of claim 22, wherein said substrate comprises a material selected from the group consisting of glass, semiconductor materials, metals, ceramics, plastics, and composites or combinations thereof.

26. The microneedle device of claim 22, wherein said hollow non-silicon microneedle comprises a metal material selected from the group consisting of nickel, copper, gold, palladium, titanium, chromium, and alloys or combinations thereof.

27. The microneedle device of claim 22, wherein the distal end has a plurality of output ports.

28. The microneedle device of claim 22, further comprising a structural support to control penetration depth.

29. The microneedle device of claim 28, wherein said structural support is adapted to mechanically fix the microneedle device to a surface that is penetrated by said hollow non-silicon microneedle.

30. A method of fabricating a microneedle, comprising:
providing a substrate with a substantially planar first surface;
depositing a metal material on said substantially planar first surface to form one or more bottom walls for one or more microneedles;
coating a top surface of said one or more bottom walls with a photoresist layer to a height corresponding to a selected inner height of a microchannel for said one or more microneedles;
depositing a metal material to form side walls and a top wall upon said one or more bottom walls and around said photoresist layer; and
removing said photoresist layer from said microchannel of said one or more microneedles; wherein said one or more microneedles are formed on said substantially planar first surface of said substrate and extend in a direction substantially parallel to said substantially planar first surface.

31. The method of claim 30, wherein the metal material is deposited by an electroplating process.

32. The method of claim 30, wherein the metal material is selected from the group consisting of palladium, titanium, chromium, nickel, gold, copper, and alloys thereof.

* * * * *

UNITED STATES PATENT AND TRADEMARK OFFICE
CERTIFICATE OF CORRECTION

PATENT NO. : 7,048,723 B1
APPLICATION NO. : 09/787498
DATED : May 23, 2006
INVENTOR(S) : Frazier et al.

It is certified that error appears in the above-identified patent and that said Letters Patent is hereby corrected as shown below:

Title page item (57)
Abstract, line 12, change "on" to --one--

Column 7
Line 24, after "The" insert --needle array device 74 can then be disposed in a machined interface structure 76 such as--

Column 8
Line 28, before "to have", remove [to have]
Line 36, change "one dimensional" to --one-dimensional--

Column 9
Equation (2), line 25, change " $\frac{\partial^2 V}{\partial x^2} \cdot \frac{\partial^2 V}{\partial y^2} - \frac{1}{\mu} \nabla p = 0$ " to -- $\frac{\partial^2 V}{\partial x^2} + \frac{\partial^2 V}{\partial y^2} - \frac{1}{\mu} \nabla p = 0$ --

Column 10
Line 28, change ", while" to --. While--

Signed and Sealed this

Twenty-fourth Day of November, 2009

David J. Kappos
*Director of the United States Patent and Trademark Office*